United States Patent [19]

Pepe et al.

[11] 3,963,726

[45] June 15, 1976

[54] QUATERNARY AMMONIUM SALTS OF CHLOROMETHYLATED SILICON COMPOUNDS

[75] Inventors: Enrico James Pepe, Amawalk; Bernard Kanner, West Nyack, both of N.Y.

[73] Assignee: Union Carbide Corporation, New York, N.Y.

[22] Filed: Nov. 9, 1971

[21] Appl. No.: 197,112

Related U.S. Application Data

[60] Division of Ser. No. 803,973, March 3, 1969, Pat. No. 3,661,963, which is a continuation-in-part of Ser. No. 423,414, Dec. 31, 1964, abandoned.

[52] U.S. Cl. .................. 260/290 S; 260/243 B; 260/244 R; 260/279 R; 260/286 A; 260/293.53; 260/294.9; 260/302 E; 260/306.7 R; 260/307 R; 260/307 D; 260/307 H; 260/307 F; 260/286 Q; 260/296 D
[51] Int. Cl.² ............... C07D 213/20; C07D 215/10
[58] Field of Search ........... 260/290, 286, 297, 243, 260/244, 279, 286, 293.53, 294.9, 302, 306.7, 307

[56] References Cited
UNITED STATES PATENTS
2,738,290   3/1956   James ................................. 260/290

*Primary Examiner*—Harry I. Moatz
*Attorney, Agent, or Firm*—Reynold J. Finnegan

[57] ABSTRACT

Quaternary ammonium salts of chloromethylated silanes or siloxanes which contain at least one

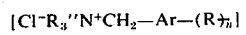

radical directly linked to a silicon atom wherein Ar is an arylene radical, wherein $R_3''N$ taken collectively is a tertiary amine radical and wherein the compounds are useful in conventional silicon applications such as anti-static agents, wetting agents, lubricants, hydraulic fluids, coating resins, elastomers and cationic surfactants.

11 Claims, No Drawings

QUATERNARY AMMONIUM SALTS OF CHLOROMETHYLATED SILICON COMPOUNDS

This application is a division of U.S. application Ser. No. 803,973, filed Mar. 3, 1969, now U.S. Pat. No. 3,661,963 which is a continuation-in-part of U.S. application, Ser. No. 423,414, filed Dec. 31, 1964, now abandoned.

This invention relates to quaternary ammonium salts of chloromethylated silicon compounds. More particularly, this invention relates to quaternary ammonium salts of chloromethylarylsilanes, chloromethylaralkylsilanes, and siloxanes produced from such silanes.

The chloromethylarylsilane quaternary ammonium salts and the chloromethylaralkylsilane quaternary ammonium salts of the instant invention can be represented by the formula

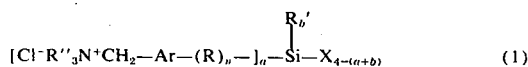  (1)

wherein Ar is an arylene radical, R is an alkylene radical, R' is a monovalent hydrocarbon radical, X is a halogen radical, preferably fluorine or chlorine, or OR' wherein R' is as defined above, $R''_3N$ taken collectively represents a tertiary amine which can be either a heterocyclic tertiary amine wherein the amino nitrogen is present in a ring structure with carbon atoms, or a tertiary amine wherein the amino nitrogen represented by N is bonded to three monovalent organic radicals represented by R'', $n$ is an integer having a value of from 0 to 1, $a$ is an integer having a value of from 1 to 3, and $b$ is an integer having a value of from 0 to 2, provided, however, that the sum of $a + b$ does not exceed 3. Preferably, $a$ has a value of 1 and the sum of $a + b$ does not exceed 2, as silanes having only a single hydrolyzable group attached to silicon are not useful in the preparation of polysiloxanes except as end-blocking units.

The arylene radicals represented by Ar in formula (1) above can be either monocyclic, bicyclic, or a fused ring, and can be unsubstituted or substituted with substituents which are inert under the reaction conditions employed in the invention. Usually such radicals have from 6 to about 18 carbon atoms. Illustrative of such radicals are o-phenylene, m-phenylene, p-phenylene, tolylene, xylylene, nitrophenylene, t-butylphenylene, naphthylene, anthrylene, methylnaphthylene, diphenylene, and the like. Preferably Ar represents a phenylene radical, most preferably p-phenylene.

The alkylene radicals represented by R in formula (1) above can be either straight or branched chain radicals, and can be unsubstituted or substituted with substituents which are inert under the reaction conditions employed in the invention. Usually such radicals have from 1 to about 12 carbon atoms, preferably from 1 to about 8 carbon atoms. Illustrative of such radicals are methylene, ethylene, propylene, isopropylene, butylene, tertiarybutylene, pentylene, 2-ethylhexylene, dodecylene, and the like.

The monovalent hydrocarbon radicals represented by R' in formula (1) can contain from 1 to 20 carbon atoms, and can be unsubstituted or substituted with substituents which are inert under the reaction conditions employed in the invention. Such radicals include straight and branched chain alkyl radicals such as methyl, ethyl, n-propyl, isopropyl, n-butyl, isobutyl, n-pentyl, n-hexyl, 2-ethylhexyl, n-decyl, n-dodecyl, n-tetradecyl, n-hexadecyl, n-octadecyl, eicosyl, and the like; alkenyl radicals such as vinyl, allyl, and the like; cycloaliphatic radicals such as cyclopentyl, cyclohexyl, and the like; aryl radicals such as phenyl, nitrophenyl, naphthyl, p-phenylphenyl, and the like; aralkyl radicals such as benzyl, β-phenylethyl, and the like; and alkaryl radicals such as p-methylphenyl, p-cyclohexylphenyl, α-methylnaphthyl, and the like. Preferably R' is an alkyl radical containing from 1 to 18 carbon atoms and most preferably from 1 to 8 carbon atoms.

The heterocyclic tertiary amines represented by $R''_3N$ in formula (1) above have a ring structure containing both nitrogen and carbon atoms in the ring, and optionally other atoms, such as oxygen. The nitrogen present in the ring makes up the tertiary amino group of the amine. The ring of the amine can be unsubstituted or substituted, provided, however, that the substituted or unsubstituted amine is inert under the reaction conditions employed in the invention except for the ability of the amine to form a quaternary compound. Such amines usually contain up to about 18 carbon atoms, preferably from 3 to about 13 carbon atoms. Illustrative of such heterocyclic tertiary amines are acridine, benzoxazole, isoquinoline, isoxazole, oxazine, oxazoline, oxazole, phenanthridine, pseudoindole, pyridine, 3-cyanopyridine, 2-ethylpyridine, 2-vinylpyridine, quinoline, quinuclidine, thiazine, thiazoline, thiazole, and the like. The most preferred quaternary compounds are pyridine and quinoline heterocyclic tertiary amines.

When $R_3''N$ of formula (1) above represents a tertiary amine wherein the amino nitrogen represented by N is bonded to three monovalent organic radicals represented by R'', the monovalent organic radicals represented by R'' contain carbon and hydrogen atoms, and optionally other atoms, such as oxygen, provided, however, that the resulting amine is inert under the reaction conditions employed in the invention except for the ability of the amine to form a quaternary compound. Such radicals include straight and branched chain alkyl radicals such as methyl, ethyl, methacryloxyethyl, acryloxyethyl, n-propyl, isopropyl, n-butyl, isobutyl, n-pentyl, n-hexyl, n-heptyl, 2-ethylhexyl, n-decyl, n-dodecyl, n-tetradecyl, n-hexadecyl, n-octadecyl, and the like; alkenyl radicals such as vinyl, allyl, and the like; cycloaliphatic radicals such as cyclopentyl, cyclohexyl, and the like; aryl radicals such as phenyl, nitrophenyl, naphthyl, p-phenylphenyl, and the like; aralkyl radicals such as benzyl, β-phenylethyl, and the like; alkaryl radicals such as p-methylphenyl, p-cyclohexylphenyl, α-methylnaphthyl, and the like. Preferably each R'' is a monovalent hydrocarbon radical having from 1 to 18 carbon atoms and most preferably an alkyl radical from 1 to 8 carbon atoms.

The chloromethylarylsilane quaternary ammonium salts and the chloromethylaralkylsilane quaternary ammonium salts of the instant invention are produced by reacting a tertiary amine of formula $R''_3N$ as described above with a chloromethylarylsilane or a chloromethylaralkylsilane represented by the formula

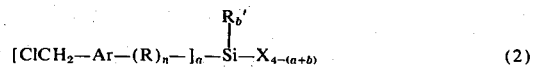  (2)

wherein Ar, R, R', X, $n$, $a$ and $b$ are as above defined.

Silanes corresponding to formula (2) above wherein X is halogen or OR''', and R''' is an alkyl radical, can be produced by reacting a suitable arylsilane or aralkylsilane with chloromethyl methyl ether and thionyl chloride, optionally in the presence of a catalytic amount of zinc chloride, at temperatures of from about 35°C. to about 120°C., to effect chloromethylation of the aryl radical of the silane, as disclosed in copending application Ser. No. 422,495, filed concurrently herewith, now U.S. Pat. No. 3,413,329, which disclosure is incorporated herein by reference.

When X is a halogen other than fluorine in formula (2) above, it is possible to readily replace such halogen with OR' groups, wherein R' is a monovalent hydrocarbon radical as defined above with reference to formula (2), by reacting the silane with a compound of the formula (3)    R' — OH wherein R' is as above defined. Although the reaction wherein the halogen atoms are replaced with OR' groups is spontaneous and proceeds without benefit of a catalyst even at room temperature, a small amount of an acid acceptor such as triethylamine can be employed to effect the removal of the last traces of halogen. Preferably, a 10 mole percent excess of R' — OH is employed.

When X is fluorine in formula (2) above, it is possible to replace such fluorine atoms with OR' groups, wherein R' is as defined above, by the catalyzed redistribution of silicone-fluorine and silicon-hydrocarbyloxy bonds as described in copending application Ser. No. 313,442, filed Oct. 3, 1963, now U.S. Pat. No. 3,374,247, which disclosure is incorporated herein by reference. In accordance with that technique, a fluorosilane is heated in contact with a silicon compound (preferably a silane) containing at least one, and preferably at least three, hydrocarbyloxy groups directly attached to silicon, and with a redistribution catalyst such as tetrabutyltitanate, aluminum trichloride, tin dichloride, zirconium tetraethoxide, and the like, to effect redistribution of the silicon-fluorine and silicon-hydrocarbyloxy bonds.

Thus, by following the procedures outlined above, it is possible to produce all the silanes of formula (2) above which are useful in the instant invention.

Quaternary ammonium salts of chloromethylarylsilanes and chloromethylaralkylsilanes are produced according to the instant invention by reacting a silane of formula (2) above with a tertiary amine of formula R''$_3$N as described above. While it is preferable to use an excess of the amine, for example an excess of from about 5 mole percent to about 100 mole percent stoichiometric equivalent of chloromethylaryl of chloromethylaralkyl group [ClCH$_2$-Ar-(R)$_{\overline{n}}$] of the silane to be quaternized, an equivalent amount of the amine can also be employed.

While, in general, temperatures of from about 15°C. to about 250°C. can be employed in preparing the desired quaternary ammonium salts of the instant invention, the preferred temperature is dependent upon the basicity and steric configuration of the amine employed. Temperatures of from about 80°C. to about 150°C. are preferred for amines having low basicity (such as pyridine, quinoline, and the like), and temperatures of from about 150°C. to about 250°C. are preferred from amines having bulky organic groups (such as triallylamine, trioctadecylamine, and the like).

Atmospheric pressure is usually employed in effecting reaction as a matter of convenience. However, if desired, subatmospheric or superatmospheric pressures can also be employed.

The chloromethylarylsilane quaternary ammonium salts and the chloromethylaralkylsilane quaternary ammonium salts produced in accordance with the instant invention can be hydrolyzed and condensed in the conventional manner, either alone or together with other hydrolyzable silanes, to produce siloxanes containing at least one unit depicted by the formula

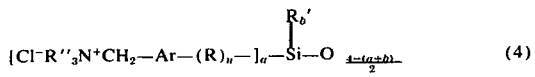    (4)

wherein R''$_3$N, Ar, R, R', n, a, and b are as above defined. When the silanes of the instant invention are cohydrolyzed and condensed with other hydrolyzable silanes, the siloxanes produced can also contain at least one unit depicted by the formula

    (5)

wherein R' is a monovalent hydrocarbon radical as defined above with reference to formula (1), and m is an integer having a value of from 1 to 3. Such siloxane units are produced by the hydrolysis of silanes of the formula (6)    R'$_m$—Si—X$_{4-m}$ wherein R' and m are as above defined, and X is halogen or OR'.

Thus, the chloromethylarylsilane quaternary ammonium salts and the chloromethylaralkylsilane quaternary ammonium salts of the instant invention can be employed to prepare siloxanes composed of units of the structure depicted by formula (4), or siloxanes composed of one or more units depicted by formula (4) and one or more units depicted by formula (5). Such siloxanes can contain up to about 5 percent by weight of hydrolyzable groups which have not been hydrolyzed.

If desired, silanes of formula (2) can be hydrolyzed and condensed either alone, or together with silanes of formula (6), to produce siloxanes which can then be treated with an amine of formula R''$_3$N, above defined with reference to formula (1), to produce the quaternary ammonium siloxanes described above. The proportions of ingredients and reaction conditions employed in producing quaternary ammonium salts of chloromethylarylsilanes and chloromethylaralkylsilanes can also be employed when a siloxane is treated with a tertiary amine to produce a quaternary ammonium siloxane.

While no solvent is necessary in effecting quaternization of silanes and siloxanes according to the instant invention, in some instances solvents such as ethanol, methanol, benzene, toluene, and the like, can be used to advantage, as for example, when only partial quaternization of a polysiloxane is desired.

The quaternary ammonium silanes and siloxanes produced in accordance with the instant invention can be purified by reprecipitation in inert solvent combinations of, for example, hexane-toluene, acetone-hexane, ethanol-toluene, methanol-isopropyl ether, and the like. However, certain of the above solvents, such as ethanol, methanol, and acetone, as well as moisture, should be avoided when groups reactive therewith are present, e.g., silicon-bonded chlorine radicals.

The silanes of the instant invention can be used in binder sizing of glass as an anti-static agent to lower the migration of binder in the winding operation; they can also be used to control electrical conductivity of mineral filled polymers by treating the filler with the silane and bonding the hydrolyzate of silane to the filler surface or by premixing the silane in the polymer prior to incorporation of the filler; they can also be used to change the wettability of the filler in polymers and polymer containing emulsions. In addition the silanes can be used to prepare the siloxane polymers disclosed herein. The siloxanes of the instant invention are useful as cationic surfacts and also in conventional siloxane applications, including uses as lubricants, hydraulic fluids, coating resins for metals and fibers, and elastomers. The siloxane polymers of this invention are also useful as lubricant additives in the treatment of inorganic oxide surfaces, such as glass, glass fibers and other siliceous substrates to impart lubricity and to improve their processing characteristics.

The following examples are illustrative of the present invention and are not to be regarded as limitative. It is to be understood that all parts, percentages and proportions referred to herein are by weight unless otherwise indicated.

EXAMPLE 1

To a 6-inch test tube were charged 11.7 grams (0.05 mole) of beta-(chloromethylphenyl)ethylmethyldifluorosilane and 5.6 grams (0.055 mole) of triethylamine, causing an immediate reaction. The tube was sealed with a glass stopper and heated at a temperature of 90°C. for 1 hour. At the end of this time, the mixture was heated to 150°C. and maintained at this temperature for 2 minutes. Following this, the mixture was stripped under vacuum, leaving 10 grams of a salt-like residue of $Cl^-Et_3N^+CH_2\phi CH_2CH_2SiMeF_2$. This represented a yield of 60 percent by weight. The product was purified by extraction with anhydrous ethyl ether. The purified product was a white, powdery, hydroscopic, water-soluble salt which had a white, powdery, hydroscopic, water-soluble salt which had a neutralization equivalent of 168 (theoretical = 171).

Analysis. Calculated for $C_{16}H_{28}SiNF_2Cl$: C, 57.2%; H, 8.4%; Si, 8.4%; N, 4.2%; F, 11.3%; Cl, 10.6%. Found: C, 56.0%; H, 8.5%; Si, 7.0%; N, 4.3%; F, 8.4%; Cl, 12.0%.

EXAMPLE 2

To a 6-inch test tube were charged 13.4 grams (0.05 mole) of chloromethylneophyltrifluorosilane and 5.6 grams (0.055 mole) of triethylamine, causing an immediate reaction. The tube was sealed and heated at a temperature of 90°C. for 1 hour. At the end of this time, the mixture was heated to 150°C. and maintained at this temperature for 2 minutes under vacuum. The residue, a dark salt weighing 9.4 grams, represented a 50 percent by weight yield of $Cl^-Et_3N^+CH_2\phi C(CH_3)_2CH_2SiF_3$. The product was purified by precipitation from acetone with diethyl ether. The purified product was a white, water-soluble salt.

Analysis. Calculated for $C_{17}H_{29}SiNF_3Cl$: Cl, 9.6%; F, 15.5%; Si, 7.6 Found: Cl, 11.8%; F, 12.5%; Si, 7.7%.

EXAMPLE 3

A mixture of beta-(chloromethylphenyl)ethyltriethoxysilane and a 50 percent molar excess of triallylamine was dissolved in 2 volumes of ethanol, and the solution was heated in a sealed pressure vessel at a temperature of 250°C. for 4 hours. The solution was then stripped under vacuum, and a dark brown residue of $Cl^-(CH_2\!\!=\!\!CHCH_2)_3N^+CH_2\phi CH_2CH_2Si(OEt)_3$ was recovered. The product was soluble in water, and a mixture acetone and water, but was insoluble in pentane, ethyl acetate, and isopropyl ether.

EXAMPLE 4

To a 250-milliliter distillation flask were charged 33 grams (0.1 mole) of beta-(chloromethylphenyl)propyltriethoxysilane, 17 grams (0.11 mole of dimethylaminoethylmethacrylate, and 0.5 gram of Ionol (an anti-oxidant). The mixture was heated at a temperature of 150°C. for 15 minutes, extracted with five 100-milliliter portions of hexane, and dissolved in 200 milliters of toluene. Hexane was then added to the solution to precipitate $Cl^-CH_2\!\!=\!\!C(CH_3\text{-})COOCH_2CH_2N^+(CH_3)_2CH_2\phi C(CH_3)HCH_2Si(OEt)_3$. The product was purified by precipitation from toluene with diethyl ether to give 40.6 grams of a dry white powder, representing a yield of 84 percent by weight. The purified product had a melting point of 90°–92°C., a bromine number of 32 (theoretical=32.7), was soluble in hot toluene, water, ethanol and acetone, and insoluble in hexane and diethyl ether.

Analysis. Calculated for $C_{24}H_{42}SiO_5NCl$: C, 59.1%; H, 8.7%; Si, 5.8%; Cl, 7.3%; N, 2.9%. Found: C, 56.9%; H, 8.5%; Si, 5.7%; Cl, 7.8%; N, 2.5%.

EXAMPLE 5

To a 200-milliliter flask were charged 16.5 grams (0.05 mole) of beta-(chloromethylphenyl)propyltriethoxysilane and 7.9 grams (0.10 mole) of pyridine. The mixture was refluxed for 45 minutes and stripped of volatiles. The residue was dissolved in toluene, and diethyl ether was then added to the solution to precipitate $Cl^-C_5H_5N^+CH_2\phi C(CH_3)HCH_2Si(OEt)_3$ in quantitative yields. The product was a light yellow resin which had a softening point of 50°C., was soluble in water and acetone, and insoluble in diethyl ether.

Analysis. Calculated for $C_{21}H_{32}SiO_3NCl$: C, 61.5%; H, 7.9%; Si, 6.8%; Cl, 8.6%; N, 3.4%. Found: C, 59.3%; H, 7.4%; Si, 7.1%; Cl, 10.2%; N, 2.0%.

EXAMPLE 6

To a 100-milliliter flask were charged 30 grams of a methylsiloxane fluid modified with silicon-bonded beta-(chloromethylphenyl)propyl groups, and 30 milliliters of methanol. A dry-ice condenser was attached to the flask, an excess of trimethylamine was added, and the mixture was refluxed for 5 minutes until homogeneity resulted. The mixture was then stripped under vacuum. The residue contained quaternized ammonium groups formed by the reaction of the trimethylamine and the beta-(chloromethylphenyl)propyl groups of the methylsiloxane.

The product can be illustrated as a linear siloxane copolymer of the formula

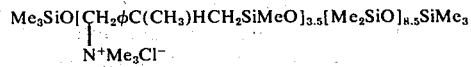

wherein Me represents a methyl radical and φ represents a phenyl radical. The siloxane had surface active properties and was useful as a surfactant.

When an excess of pyridine was reacted with the methylsiloxane fluid in a similar manner in a sealed tube at 160°C. for 48 minutes, a pyridinium quaternary derivative was obtained. This product also had surface active properties and was useful as a surfactant and may be illustrated by the formula

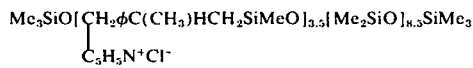

wherein Me and φ are the same as defined above.

methylamine until quaternization was completed. Reaction was judged complete when a clear 1 wt.% solution of the total mixture in water was obtained, usually after 15 minutes. Vacuum stripping at 100°C. to 1 mm. of mercury pressure produced a clear, colorless homogeneous silicone copolymer characterized by the formula

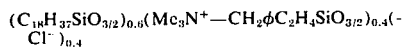

having the indicated mole fraction of cationic groups.

Cationic silicone copolymers containing 20, 10, 5 and 2.5 mole-% of quaternary ammonium grouping were also prepared. Physical properties and elemental analyses for the complete series are summarized in Table I, below.

TABLE I

PHYSICAL PROPERTIES OF
$(C_{18}H_{37}SiO_{3/2}) \times (Me_3N^+CH_2\phi C_2H_4SiO_{3/2})$ y Cl⁻y
CATIONIC SILICONE COPOLYMERS (x + y = 100 mole - %)

| Composition (Mole-% of y) | m.p.°C. | *Solubility (1 wt.-% in H₂O) | %Si/ Calc. | %N/ Calc. | %Cl/ Calc. |
|---|---|---|---|---|---|
| 40 | 44–45 | Soluble | 8.6/9.6 | 1.56/1.92 | 4.2/4.86 |
| 20 | 45–46 | Disperses | 8.4/9.5 | 0.73/0.96 | 2.1/2.43 |
| 10 | 44–45 | Disperses | 8.2/9.4 | 0.40/0.48 | 1.1/1.21 |
| 5 | 51–52 | Disperses | 8.4/9.3 | 0.30/0.24 | 0.6/0.60 |
| 2.5 | 54–55 | Disperses | 8.4/9.3 | 0.14/0.12 | 0.3/0.30 |
| 0 | 56–57 | Insol. ppt. | — | — | — |

*Added to 60°C. water as 6 wt.-% solution in isopropanol.

EXAMPLE 7

Other quaternary ammonium compounds can be prepared by following the procedure outlined in Examples 1 to 6 of reacting one mole of the silane reactant with a slight molar excess of amine and replacing the above amine reactants with other amines such as, trimethylamine, methyldiethylamine, methyldioctadecylamine, phenyldimethylamine, phenyldiethylamine, tripropylamine, trioctadecylamine, trioctylamine, 2-ethylpyridine, quinoline, and the like and/or replacing the silane reactant with other silanes such as, beta-(chloromethylphenyl)propylmethyldichlorosilane, chloromethylneophyltrichlorosilane, beta-(chloromethylphenyl)propyltrichlorosilane, beta-(chloromethylphenyl)propyltrifluorosilane, beta-(chloromethylphenyl)-ethyltrifluorosilane, beta-(chloromethylphenyl)octyltrifluorosilane, beta-(chloromethylphenyl)propylmethyldifluorosilane, beta-(chloromethylphenyl)propyloctadecyldifluorosilane, beta-(chloromethylphenyl)propyltrimethoxysilane, beta-(chloromethylphenyl)propylmethyldiethoxysilane, beta-(chloromethylphenyl)-propyloctadecyldiethoxysilane and the like.

EXAMPLE 8

Into a 100 ml., 3-necked flask, outfitted with mechanical stirrer, thermometer, water condenser and heating mantle was charged 11.2 grams (0.03 moles) of $C_{18}H_{37}Si(OMe)_3$, 5.4 grams, 0.02 moles of $ClCH_2\phi C_2H_4Si(OMe)_3$, of approximately equal parts and 18 grams of isopropanol. The stirred mixture was heated to reflux, whereupon dropwise addition of 1.35 grams of 0.1 NHCl was made over about 1 minute. The mixture was heated at reflux of ½ hour, followed by a 1-liter per minute sparge, at reflux, with gaseous tri- The siloxane copolymers are especially useful as glass fiber production lubricants and can be used alone or as additives to conventional forming size compositions.

Other copolymers can be prepared by employing approximately the same mole ratio of ingredients as outlined above, but replacing the octadecyltrimethoxysilane with other silanes such as methyltrimethoxysilane, ethyltrimethoxysilane, octadecyltriethyloxysilane, eicosyltrimethoxysilane, and the like; and/or replacing (chloromethylphenyl)ethyltrimethoxysilane with other silanes such as (chloromethylphenyl)propyltrimethoxysilane, chloromethylneophyltrimethoxysilane, and the like; and/or replacing trimethylamine with other amines such as, triethylamine, triallylamine, dimethylaminoethylmethacrylate, pyridine, methyldiethylamine, methyldioctadecylamine, phenyldimethylamine, phenyldiethylamine, tripropylamine, trioctadecylamine, trioctylamine, 2-ethylpyridine, quinoline, and the like.

Various modifications and variations of this invention will be obvious to a worker skilled in the art and it is understood that such modifications and variations are to be included within the purview of this application and the spirit and scope of the appended claims.

What is claimed is:

1. A quaternary ammonium salt selected from the group consisting of (A) silanes represented by the formula

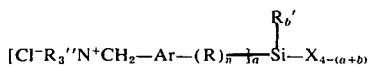

wherein Ar is a phenylene radical, R is an alkylene radical having from 1 to 8 carbon atoms; R' is an alkyl radical having from 1 to 20 carbon atoms, X is a radical selected from the group consisting of chlorine, fluorine and OR' wherein R' is as defined above; $R_3''N$ taken collectively represents a heterocyclic tertiary amine containing from 3 to 13 carbon atoms wherein the amino nitrogen represented by N is the nitrogen atom in said heterocyclic radical; $n$ has a value of from 0 to 1; $a$ is an integer having a value of from 1 to 3; and $b$ has a value of from 0 to 2, provided, however, that the sum of $(a+b)$ does not exceed 3; and (B) siloxanes consisting of at least one siloxy unit represented by the formula

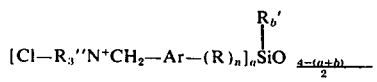

wherein Ar, R, R', $R_3''N$, $n$, $a$, $b$, and $(a+b)$ are the same as defined above; and at least one siloxy unit represented by the formula

wherein R' is the same as defined above and $m$ is an integer from 1 to 3.

2. A quaternary ammonium salt of a silane as defined in claim 1, wherein the heterocyclic tertiary amine is selected from the group consisting of pyridine and quinoline; $a$ is 1 and the sum of $(a+b)$ does not exceed 2.

3. A quaternary ammonium salt of a silane as defined in claim 1, wherein $n$ is 1 and the heterocyclic tertiary amine is pyridine.

4. A quaternary ammonium salt of a siloxane as defined in claim 1, wherein the heterocyclic tertiary amine is selected from the group consisting of pyridine and quinoline.

5. A quaternary ammonium salt of a siloxane as defined in claim 4, wherein $n$ is 1 and the heterocyclic tertiary amine is pyridine.

6. A quaternary ammonium salt as defined in claim 3, wherein X is fluorine.

7. A quaternary ammonium salt as defined in claim 3, wherein X is chlorine.

8. A quaternary ammonium salt of a silane as defined in claim 3, wherein X is OR' and R' represents an alkyl radical having from 1 to 8 carbon atoms.

9. A quaternary ammonium salt of a siloxane as defined in claim 5, wherein R' is an alkyl radical selected from the group consisting of methyl and octadecyl radicals.

10. A quaternary ammonium salt represented by the formula

wherein $\phi$ represents a phenylene radical.

11. A quaternary ammonium salt represented by the formula

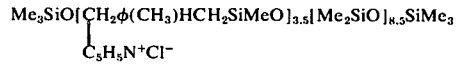

wherein Me represents a methyl radical and $\phi$ represents a phenylene radical.

* * * * *

UNITED STATES PATENT OFFICE
CERTIFICATE OF CORRECTION

Patent No. 3,963,726                    Dated June 15, 1976

Inventor(s)  E. J. Pepe et al

It is certified that error appears in the above-identified patent and that said Letters Patent are hereby corrected as shown below:

Column 5, lines 46-47, delete the phrase "a white, powdery, hydroscopic, water-soluble salt which had".

Column 5, line 68 (last line) after "7.6" insert ---%---.

Signed and Sealed this

Eleventh Day of January 1977

[SEAL]

Attest:

RUTH C. MASON
Attesting Officer

C. MARSHALL DANN
Commissioner of Patents and Trademarks